United States Patent [19]

Greco

[11] Patent Number: 4,731,461

[45] Date of Patent: Mar. 15, 1988

[54] PROCESS FOR PREPARING TIN ALKOXIDES

[75] Inventor: Carl C. Greco, Garnerville, N.Y.

[73] Assignee: Stauffer Chemical Company, Westport, Conn.

[21] Appl. No.: 872,329

[22] Filed: Jun. 9, 1986

[51] Int. Cl.[4] .................... C07F 7/22

[52] U.S. Cl. .................... 556/81

[58] Field of Search .................... 556/81

[56] References Cited

U.S. PATENT DOCUMENTS

| | | | |
|---|---|---|---|
| 2,269,498 | 1/1942 | Wainer | 556/81 X |
| 2,684,972 | 7/1954 | Haslam | 556/81 |
| 2,901,452 | 8/1959 | West | 556/81 X |
| 3,256,188 | 6/1966 | Papayannopoulos et al. | 556/81 X |
| 3,306,926 | 2/1967 | Neher et al. | 556/81 X |
| 3,641,077 | 2/1972 | Rochow | 556/81 |
| 3,931,260 | 1/1976 | Foley et al. | 556/81 X |
| 3,946,056 | 3/1976 | Thomas | 556/81 |

*Primary Examiner*—Helen M. S. Sneed

[57] ABSTRACT

Tin tetra-alkoxides absent halogenic impurities are prepared by a two-step process comprising a first step reaction of tin tetrahalide with an alcohol and ammonia. A second step reacts the product of the first step with a metal amide and additional alcohol. An alternative second step reacts the product of the first step with a metal alkoxide.

15 Claims, No Drawings

PROCESS FOR PREPARING TIN ALKOXIDES

FIELD OF THE INVENTION

This invention is a process for preparing tin alkoxides.

BACKGROUND OF THE PRESENT INVENTION

Tin alkoxides have been prepared by a variety of means, however, purification problems are inherent in many of the known procedures.

Bradley (Journal of Chemical Society 1957, pages 4775, 4777, and Progress in Inorganic Chemistry, 2, 1960, page 303) teaches the preparation of tin alkoxides from the reaction of stannic chloride, ethyl alcohol, and amnonia. The Bradley product had an analysis of Sn, 39.6%; EtO, 50.8%; $NH_3$, 5.1%; and Cl, 3.5%.

Typically, from 2 to 5% chlorine remains in the product and is very difficult to remove.

It is desirable to develop a process for preparing tin tetra-alkoxides so that even minor levels of residual halogen are removed. Pure tin tetra-alkoxides may be hydrolyzed to prepare pure tin oxides and hydroxides useful as coatings on glass.

SUMMARY OF THE INVENTION

This invention is a two-step process for preparing tin alkoxides. The first process step reacts a tin halide, an alcohol, and ammonia to form a product represented on the average by the formula:

$$(R_1O)_{4-m}SnX_m$$

wherein $R_1$ is an organo- radical derived from the alcohol and X is a halogen derived from the tin halide and m is a number between about 0.1 and about 1.0. A second process step reacts the halogenated tin alkoxide product of step 1 with (i) a metal amide and an alcohol, or (ii) an alkali metal oxide, to form a tin tetra-alkoxide having substantially no chlorine (viz., less than 0.1% chloride ion).

DETAILED DESCRIPTION OF THE INVENTION

The process of the invention has two essential steps.

The First Process Step:

The first process step reacts a (1) tin halide, (2) an alcohol, and (3) ammonia as represented by the following chemical equation:

$$SnX_4+4R_1OH+4NH_3\rightarrow(R_1O)_{4-m}SnX_m+NH_4X$$

wherein m varies from about 0.1 to about 1.0, $R_1$ is a alkyl or alkoxyalkyl group and X is a halogen.

The tin tetrahalide reactant is selected from tin tetrachloride, tin tetrabromide, tin tetraiodide or mixtures thereof.

The alcohol reactant may be a simple alcohol represented by the formula:

$$R_1—OH$$

or an alkoxy alcohol represented by the formula:

$$R_1O—(CH_2)_p—OH$$

wherein for the simple or alkoxy alcohols $R_1$ is an organo- group and p is a positive integer from 1 to 12.

The alcohol reactant of the first step may be a primary, secondary or tertiary alcohol. $R_1$ is preferably an alkyl radical of 1 to 12 carbon atoms. Most preferred are alcohols wherein $R_1$ has 1 to 4 carbon atoms and p has a value from 1 to 4. Examples of alcohols having utility in the first process step are ethanol, isopropanol, n-butanol, 2-methoxy ethanol, 3-ethoxy propanol, 3-methoxy butanol, or mixtures thereof.

The alcohol reactant of the first step may be used in stoichiometric excess to form the reaction medium of the invention. Alternatively, inert solvents such as benzene, toluene, xylene, octane, or cyclohexane may be used as solvent or cosolvent in the first step reaction medium.

The ammonia reactant is provided as a gas sparged into the reactor zone. Preferably, the ammonia reactant is sparged into the reaction medium until substantially all of the ammonium halide is formed.

The ratio of reactants in the first step are not critical. Usually, an excess of alcohol reactant is present to fulfill the additional function of a liquid solvent reaction medium. Moreover, the ammonia reactant is typically supplied in stoichiometric excess since it is difficult to know precisely how much gaseous ammonia is retained in the liquid reaction zone.

The time and temperature of the first step reaction are not critical. Temperatures ranging from ambient (20° C.) to the reflux temperature of the reaction medium (viz., 70° C. to 150° C.) are employed. The first step reaction is generally completed in 1/4 to 6 hours.

Partial purification of the first step reaction product is necessary to remove as much as possible the ammonium halide by-product from the $(R_1O)_{4-m}SnX_m$ reaction product. The reaction product is cooled and filtered to remove ammonium halide by-product. Cosolvents such as toluene may be added, if desired, to encourage the precipitation of ammonia halides. Excess solvent may be removed from the step procedure by stripping. There will remain in the first step reaction product a residual halide content of from about 2% to about 5% that cannot be removed by conventional washing, stripping or other procedures.

The phrase, "residual halide" for the purposes of the invention refers to halogen determined by dispersing a product in water and testing for the presence of chloride, bromide, or iodide ion by any suitable analytical method. Chloride ion is conveniently determined by silver nitrate titration.

The Second Reaction Step:

It is a discovery of this invention that a second step reaction may be used to substantially remove the residual halide from the first step alkoxy tin halide reaction product. There are two alternative procedures suitable for the second step conversion to tin tetraalkoxides. These alternative procedures are hereinafter referred to as "Step 2A" and "Step 2B".

Step 2A Method:

The first step reaction product, $$(RO_1)_{4-m}SnX_m$$

is redissolved in a solvent and thereafter reacted with a metal amide reactant and an alcohol reactant as represented by the following chemical equation:

$$(R_1O)_{4-m}SnX_m+m(M(NH_2)_q)+m(R_1O—OH)\rightarrow(R_1O)_4Sn+mM(X)_q+mNH_3$$

wherein $R_1$, X, and m are as previously defined and q is an integer corresponding to the valence of the metal, M.

The metal halide salt $M(X)_q$ is removed typically by adjusting the composition of the reaction medium to cause its selective precipitation. For example, when $M(X)_q$ is NaCl then the addition of toluene to a predominantly alcoholic reaction medium will encourage NaCl precipitation.

The second step amide reactant, $M(NH_2)_q$ has a value of q from 1 to 2. Preferably, the value of q is one and is inclusive of using sodium amide, lithium amide, potassium amide and mixtures thereof.

The second step alcohol reactant $R_1$—OH is usually identical with the alcohol employed in the first step reaction. Use of the same alcohol in the second step insures that the additional $R_1$ groups substituted for the expelled halogen will be the same as those present in the first step product. However, if desired, a different alcohol reactant may be used in the second step to give a tin alkoxide with mixed hydrocarbyl groups.

Steps 2A and 2B may, in all instances, use the alkoxy alcohol reactant, $R_1O—(CH_2)_p—OH$, in place of the simple alcohol $R_1$—OH.

The time and temperature requirements for reaction are the same as those set out for the first step reaction. Ratios of the reactants are not critical, although the alcohol reactant is typically used in excess to serve as reaction medium.

Step 2B Method:

The second step of the process may alternatively be conducted by the reaction of the first step reaction product with a metal alkoxide as represented by the following chemical equation:

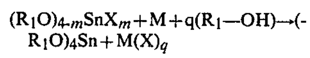

$$(R_1O)_{4-m}SnX_m+M+q(R_1—OH)\rightarrow(R_1O)_4Sn+M(X)_q$$

where $R_1$, X, and m are as previously defined and q is an integer corresponding to the valence of the metal, M.

The alcohol reactive metal M and the alcohol $R_1$—OH are reacted together prior to introducing the halogenated tin alkoxide of the first step product into the reaction zone. The termination of the reaction may be judged from the cessation of hydrogen evolution. The resultant soluble metal alkoxide, $M(OR_1)_q$, is preferably an alkoxide of a monovalent metal such as sodium, lithium or potassium.

The first step reaction product is reacted with the metal alkoxide to give a halogen-free tin tetra-alkoxide final product.

The time and temperature of reaction are not critical and are the same as for Step 2A. The alkoxide reactant is typically used in about stoichiometric proportions with the first step reaction product. The reaction medium is advantageously an alcohol or alcohol with a cosolvent such as benzene, toluene or tetrahydrofuran (THF).

Purification of the final product in Steps 2A or 2B is accomplished by solvent stripping, if desired.

EXAMPLE 1

Part A

In a 500 ml. 3-neck flask was dissolved 48 grams of isopropanol in 350 cc. of toluene. To this was added at room temperature 50 grams of $SnCl_4$ (0.192 moles). The reaction was only slightly exothermic and no HCl was given off. Ammonia gas was passed through the solution for four hours during which $NH_4Cl$ formed and the reaction temperature rose to 80° C. The reaction mixture was refluxed for one hour under a $NH_3$ purge. The mixture was cooled to room temperature and filtered. The filtrate was stripped to constant weight and yielded a solid (52.3 grams). This solid product weighed 75% of the theoretical yield of tin tetra-isopropoxide. Analysis for ionic chloride was done by $AgNO_3$ titration. The product contained 3% chloride ion which correspond to 28% $(C_3H_7O)_3SnCl$ and 72% $(C_3H_7O)_4Sn$, represented by an average molecular formula of $(C_3H_7O)_{3.72}SnCl_{0.28}$.

Part B

The reaction product of Part A was dissolved in 200 cc. of toluene.

A solution of $NaNH_2$ (3 grams) in 50 cc. of tetrahydrofuran and 25 cc. of isopropyl alcohol were added. The resulting solution was refluxed for 4 hours during which time $NH_3$ gas came from the reaction. After the reflux period, the reaction mixture was filtered and the filtrate stripped to dryness. A solid product remained at 75% theoretical yield. Analysis for Tin—35.2% found, 33.5% theor. calc. Analysis Chloride Ion—0.06% found.

EXAMPLE 2

Same procedure as Example 1, only 55.3 grams of methoxyethanol was used as the alcohol. The yield of product (Step 1) was 72% and the ionic chloride analysis showed 0.7% Cl. This product's composition was 6.8% $(CH_3OCH_2CH_2O)_3SnCl$ and 93.2% $(CH_3OCH_2CH_2O)_4Sn$. Treatment with $NaNH_2$ in tetrahydrofuran gave 100% yield with no detectable chloride. The overall yield of $(CH_3OCH_2CH_2O)_4Sn$ was 72%.

EXAMPLE 3

3.3 grams of sodium metal was dissolved in 200 cc. of isopropanol. Heat was applied to complete the reaction. The freshly prepared solution of sodium isopropoxide was mixed with 91 grams (dissolved in 400 ml. toluene) of the halogenated tin alkoxide product prepared in Part A of Example 1.

The resulting mixture was refluxed for 4 hours. The reaction mixture was filtered and the filtrate stripped to dryness of flash evaporator.

Actual yield of product was 94 grams. Theoretical yield for $(C_3H_7O)_4Sn$ is 95.24 grams.

A silver nitrate test showed no detectable chloride ion.

Analysis for Tin 30.3% found 33.5% theor. calc. Yield based on analysis was 85 grams or 89% yield.

We claim:

1. A process for the preparation of tin tetraalkoxides which comprises the following steps:

(a) combining in a liquid reaction medium a tin tetrahalide reactant, a first step alcohol reactant, and an ammonia reactant, to yield a halogen containing tin alkoxide product represented on the average by the formula:

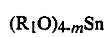

$$(R_1O)_{4-m}Sn$$

wherein $R_1$ is an alkyl or alkoxyalkyl group, X is a halogen, and m is a number from about 0.1 to about 1.0, (b) reacting the tin alkoxide reaction product of Step (a) with a metal amide reactant and a second-step alcohol reactant to yield a substantially halogen-free tin tetra-alkoxide reaction product represented by the formula:

$$(R_1O)_4Sn$$

wherein $R_1$ is as defined in Step (a).

2. The process of claim 1 wherein the tin tetrahalide is selected from tin tetrabromide, tin tetrachloride, tin tetraiodide, or mixtures thereof.

3. The process of claim 1 wherein the alcohol reactant is a primary, secondary, or tertiary alcohol.

4. The process of claim 3 wherein the first step and second step alcohol reactant is represented by the formula:

$$R_1{-}OH$$

wherein $R_1$ is an alkyl group of from 1 to 12 carbon atoms.

5. The process of claim 3 wherein the first step and second step alcohol reactant is represented by the formula:

$$R_1O{-}(CH_2)_p{-}OH$$

wherein $R_1$ is an alkyl group of from 1 to 12 carbon atoms, and p is an integer from 1 to 12.

6. The process of claim 1 wherein the first step alcohol reactant is the same as the second step alcohol reactant.

7. The process of claim 1 wherein the Step (b) metal amide reactant is selected from lithium amide, sodium amide, potassium amide, or mixtures thereof.

8. A process for the preparation of tin alkoxides which comprises the following steps:

(a) combining in a liquid reaction medium a tin tetrahalide reactant, a first step alcohol reactant, and an ammonia reactant, to yield a halogen containing tin alkoxide product represented on the average by the formula:

$$(R_1O)_{4-m}SnX_m$$

wherein $R_1$ is an alkyl or alkoxyalkyl group, X is a halogen, and m is a number from about 0.1 to about 1.0, (b) reacting the tin alkoxide reaction product of Step (a) with a metal alkoxide reactant to yield a halogen-free tin tetra-alkoxide reaction product represented by the formula:

$$(R_1O)_4Sn$$

wherein $R_1$ is as defined in Step (a).

9. The process of claim 8 wherein the tin tetrahalide is selected from tin tetrabromide, tin tetrachloride, tin tetraiodide, or mixtures thereof.

10. The process of claim 8 wherein the alcohol reactant is a primary, secondary, or tertiary alcohol.

11. The process of claim 10 wherein the first step and second step alcohol reactant is represented by the formula:

$$R_1{-}OH$$

wherein $R_1$ is an alkyl group of from 1 to 12 carbon atoms.

12. The process of claim 11 wherein the first step and second step alcohol reactant is represented by the formula:

$$R_1O{-}(CH_2)_p{-}OH$$

wherein $R_1$ is an alkyl group of from 1 to 12 carbon atoms, and p is an integer from 1 to 12.

13. The process of claim 12 wherein the first step alcohol reactant is the same as the second step alcohol reactant.

14. The process of claim 8 wherein the Step (b) metal alkoxide reactant is selected from lithium alkoxide, sodium alkoxide, or potassium alkoxide.

15. The process of claim 8 wherein the second step alkoxide reactant is prepared by the reaction of sodium metal with a primary alcohol having 1 to 12 carbon atoms.

* * * * *